(12) United States Patent
Erdman et al.

(10) Patent No.: US 7,781,583 B2
(45) Date of Patent: Aug. 24, 2010

(54) SYNTHESIS OF 2-(PYRIDIN-2-YLAMINO)-PYRIDO[2,3-D] PRYIMIDIN-7-ONES

(75) Inventors: David Thomas Erdman, Portage, MI (US); Cathlin Marie Flamme, Cincinnati, OH (US); Jade Douglas Nelson, Mystic, CT (US)

(73) Assignee: Pfizer Inc, New York, NY (US)

( * ) Notice: Subject to any disclaimer, the term of this patent is extended or adjusted under 35 U.S.C. 154(b) by 0 days.

(21) Appl. No.: 11/852,873

(22) Filed: Sep. 10, 2007

(65) Prior Publication Data

US 2008/0125588 A1  May 29, 2008

Related U.S. Application Data

(60) Provisional application No. 60/843,051, filed on Sep. 8, 2006, provisional application No. 60/942,104, filed on Jun. 5, 2007.

(51) Int. Cl.
*C07D 471/04* (2006.01)
*C07D 487/04* (2006.01)
*A61P 35/00* (2006.01)

(52) U.S. Cl. .................................................... 544/279
(58) Field of Classification Search ................... 544/279
See application file for complete search history.

(56) References Cited

U.S. PATENT DOCUMENTS 6,936,612 B2    8/2005    Barvian et al.

FOREIGN PATENT DOCUMENTS

WO    2005005426 A1    1/2005

OTHER PUBLICATIONS

Berge, S., "Pharmaceutical Salts," Journal of Pharmaceutical Sciences, 1977, v. 66, p. 1-19.

*Primary Examiner*—James O Wilson
*Assistant Examiner*—Cecilia M Jaisle
(74) *Attorney, Agent, or Firm*—Keith D. Hutchinson; Jeffrey H. Tidwell

(57) ABSTRACT

The present invention provides methods of preparing substituted 2-(pyridin-2-ylamino)-pirido[2,3-d]pyrimidin-7-ones (formula 1),

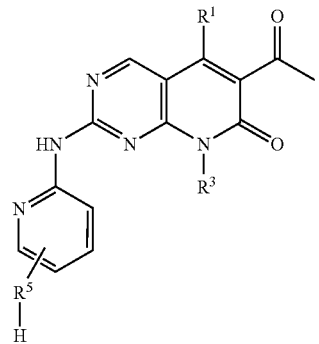

useful in treating cell proliferative disorders, or a pharmaceutically acceptable salt thereof.

2 Claims, No Drawings

SYNTHESIS OF 2-(PYRIDIN-2-YLAMINO)-PYRIDO[2,3-D] PRYIMIDIN-7-ONES

This application claims the benefit of U.S. Provisional Application No. 60/843,051 filed Sep. 8, 2006, and U.S. Provisional Application No. 60/942,104 filed Jun. 5, 2007, the contents of which are hereby incorporated by reference in their entireties.

FIELD OF THE INVENTION

This invention relates to novel synthetic routes for the preparation of substituted 2-(pyridin-2-ylamino)-pirido[2,3-d]pyrimidin-7-ones and their intermediates.

BACKGROUND

This invention relates to novel method to prepare substituted 2-(pyridin-2-ylamino)-pirido[2,3-d]pyrimidin-7-ones has the formula (herein to as "Formula 1"),

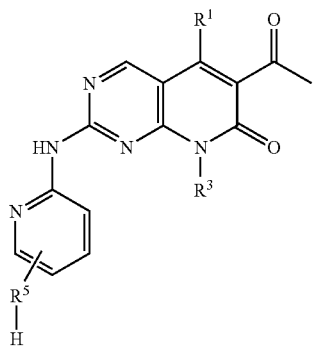

wherein $R^1$ is hydrogen, $C_1$-$C_6$ alkyl, $C_1$-$C_6$ haloalkyl, $C_1$-$C_6$ hydroxyalkyl, or $C_3$-$C_7$ cycloalkyl;

$R^3$ is hydrogen, OH, —$NH_2$, aryl, $C_1$-$C_8$ alkyl, $C_3$-$C_7$ cycloalkyl, or $C_3$-$C_7$-heterocyclyl;

$R^5$, is —$(CR^7R^8)_m NR^7$ or —$(CR^7R^8)_m$— (3 to 10 member heterocycle comprising a N ring atom), wherein m is 0, 1, 2 or 3;

and each $R^7$ and $R^8$ is independently H or $C_1$-$C_6$ alkyl;

or a pharmaceutically acceptable salt thereof.

In particular, the present invention relates to novel methods for the preparation of the isethionate salt forms of compound 6-Acetyl-8-cyclopentyl-5-methyl-2-(5-piperazin-1-yl-pyridin-2-ylamino)-8H-pyrido[2,3-d]pyrimidin-7-one hydrochloride (also referred to as "Compound 1"),

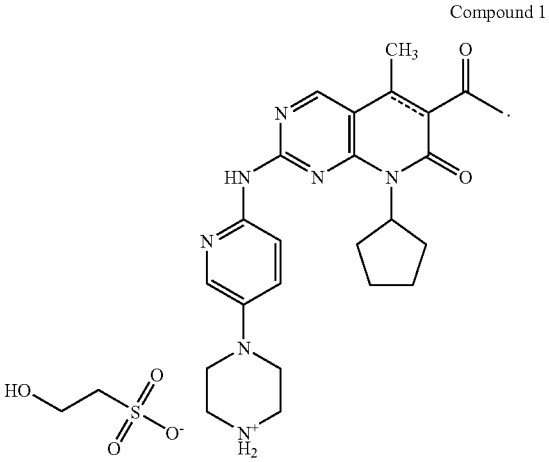

as well as its intermediates. Compound 1 is described in U.S. Pat. No. 6,936,612, the disclosure of which is hereby incorporated in its entirety. This compound is a protein kinase inhibitor and represents a synthetic, small molecule inhibitor capable of modulating cell cycle control.

A method of preparing Compound 1 is disclosed as Example 36 of U.S. patent application Ser. No. 6,936,612. Methods of preparing the isethionate salt forms of Compound 1 are disclosed in Examples 1-13 of WO 2005/005426. These methods are for synthesis of small quantities of the salt forms of Compound 1 and are not designed for commercial scale-up. Therefore, a preparation of the salt forms for CDK inhibitor 6-Acetyl-8-cyclopentyl-5-methyl-2-(5-piperazin-1-yl-pyridin-2-ylamino)-8H-pyrido[2,3-d]pyrimidin-7-one hydrochloride which is cost-efficient, scaleable and productive is highly desirable.

SUMMARY OF THE INVENTION

In one embodiment, and in combination of any other embodiments not inconsistent, this invention provides a method to prepare substituted 2-(pyridin-2-ylamino)-pirido[2,3-d]pyrimidin-7-ones has the formula (herein to as "Formula 1"),

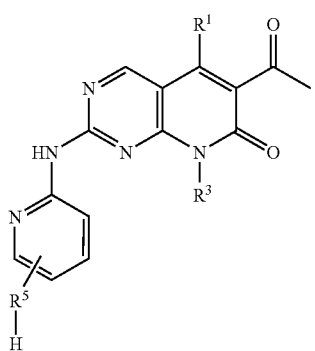

wherein $R^1$ is hydrogen, $C_1$-$C_6$ alkyl, $C_1$-$C_6$ haloalkyl, $C_1$-$C_6$ hydroxyalkyl, or $C_3$-$C_7$ cycloalkyl;

$R^3$ is hydrogen, OH, —$NH_2$, aryl, $C_1$-$C_8$ alkyl, $C_3$-$C_7$ cycloalkyl, or $C_3$-$C_7$-heterocyclyl;

$R^5$, is $-(CR^7R^8)_m NR^7-$ or $-(CR^7R^8)_m-$ (3 to 10 member heterocycle comprising a N ring atom), wherein m is 0, 1, 2 or 3;

and each $R^7$ and $R^8$ is independently H or $C_1$-$C_6$ alkyl;

or a pharmaceutically acceptable salt thereof; comprising the step of (a) reacting a compound of formula

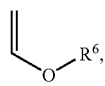

with a compound of formula Id

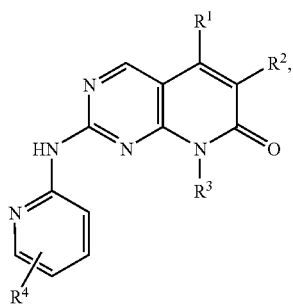

wherein:
$R^1$ is hydrogen, $C_1$-$C_6$ alkyl, $C_1$-$C_6$ haloalkyl, $C_1$-$C_6$ hydroxyalkyl, or $C_3$-$C_7$ cycloalkyl;
$R^2$ is Br or I;
$R^3$ is hydrogen, OH, $-NH_2$, aryl, $C_1$-$C_8$ alkyl, $C_3$-$C_7$ cycloalkyl, or $C_3$-$C_7$-heterocyclyl;
$R^4$ is $-R^5-$PG selected from the group consisting of $-(CR^7R^8)_m-N(PG)R^7$, and $-(CR^7R^8)_m-$ (3 to 10 member heterocycle comprising a PG protected N ring atom), and PG is an acid-labile amine protecting group;
$R^5$, being $R^4$ without the PG, is $-(CR^7R^8)_m NR^7-$ or $-(CR^7R^8)_m-$ (3 to 10 member heterocycle comprising a N ring atom), wherein m is 0, 1, 2 or 3;
$R^6$ is $C_1$-$C_6$ alkyl; and
each $R^7$ and $R^8$ is independently H or $C_1$-$C_6$ alkyl;

in the presence of a transition metal catalyst, a base and optionally a phosphine agent, and in a suitable solvent to form a compound of formula Ie or If;

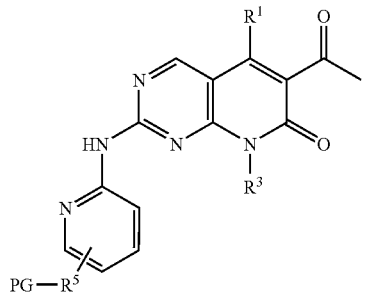

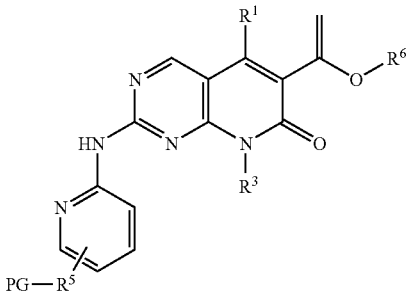

and (b1) deprotecting $R^5$ of the compound of formula Ie or If by removing PG.

In another embodiment, and in combination with any other embodiments not inconsistent, the invention provides a method of preparing a compound of formula I;

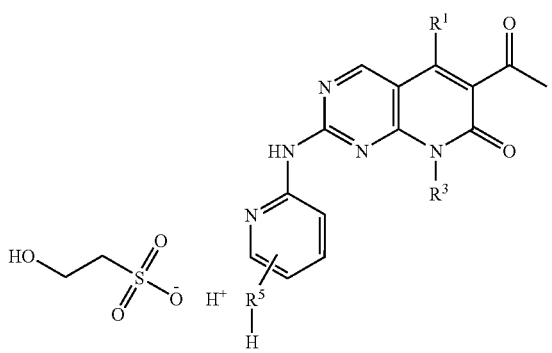

comprising the steps of
(a) reacting a compound of formula

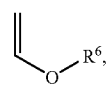

with a compound of formula Id

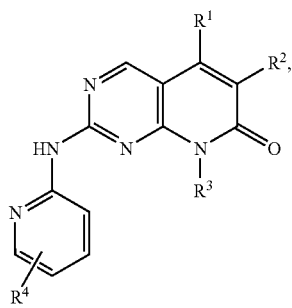

wherein:
$R^1$ is hydrogen, $C_1$-$C_6$ alkyl, $C_1$-$C_6$ haloalkyl, $C_1$-$C_6$ hydroxyalkyl, or $C_3$-$C_7$ cycloalkyl;
$R^2$ is Br or I;
$R^3$ is hydrogen, OH, $-NH_2$, aryl, $C_1$-$C_8$ alkyl, $C_3$-$C_7$ cycloalkyl, or $C_3$-$C_7$-heterocyclyl;

R⁴ is —R⁵—PG selected from the group consisting of —(CR⁷R⁸)ₘ—N(PG)R⁷, and —(CR⁷R⁸)ₘ— (3 to 10 member heterocycle comprising a PG protected N ring atom), and PG is an acid-labile amine protecting group;

R⁵, being R⁴ without the PG, is —(CR⁷R⁸)ₘNR⁷— —(CR⁷R⁸)ₘ— (3 to 10 member heterocycle comprising a N ring atom), wherein m is 0, 1, 2 or 3;

R⁶ is C₁-C₆ alkyl; and each R⁷ and R⁸ is independently H or C₁-C₆ alkyl;

in the presence of a transition metal catalyst, a base and optionally a phosphine agent, and in a suitable solvent to form a compound of formula Ie or If;

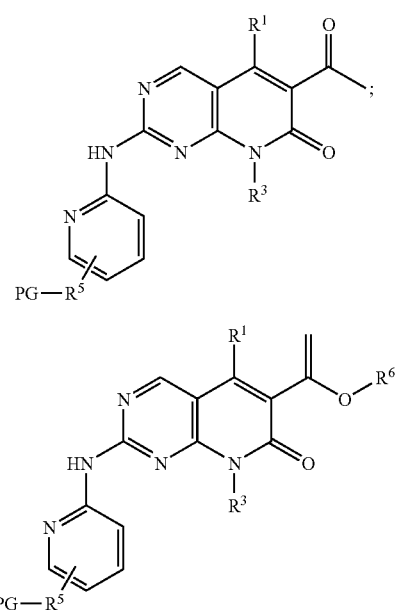

and (b) subsequently reacting the compound of formula Ie or If, or the mixture thereof, with isethionic acid in a suitable solvent to give the compound of formula I.

In one particular aspect of the embodiment, and in any other particular aspects not inconsistent, R¹ is C₁-C₆ alkyl.

In another particular aspect of this embodiment, and in combination with any other particular aspects not inconsistent, the compound of formula I is compound 1

Compound 1

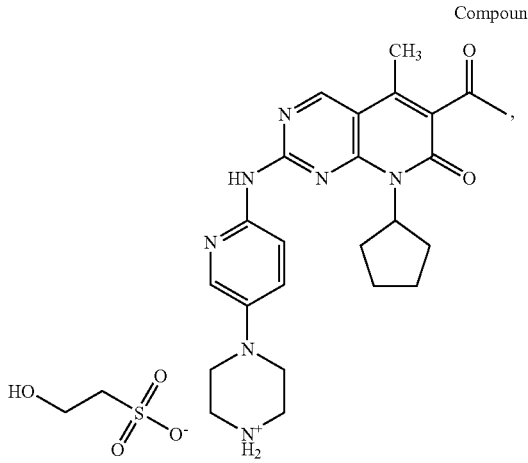

PG is Boc, and R⁶ is n-butyl.

In another particular aspect of the embodiment, and in combination with any other particular aspects not inconsistent, the transition metal catalyst in step (a) is a palladium compound selected from the group consisting of tetrakis (triphenylphosphine)palladium [(Ph₃P)₄Pd], tris(dibenzylideneacetone)dipalladium [Pd₂(dba)₃], bis(dibenzylideneacetone) palladium(0) [(dba)₂Pd], palladium acetate [Pd(OAc)₂], palladium chloride (PdCl₂), bis(benzonitrile) dichloropalladium [(C₆H₅CN)₂PdCl₂] and (Bis-(diphenylphosphinoferrocene)palladium dichloride dichloromethane complex (Pd(dppf)₂Cl₂), and the phospine compound in step (a) is selected from 2,2'-bis(diphenylphosphino)-1,1'-binaphthalene (BINAP), 1,3 bis(diphenylphosphino)propane, triphenylphosphine (Ph₃P), triorthotolylphosphine [(o-CH₃Ph)₃P] and tri-t-butylphosphine. Preferably, the transition metal catalyst is (Bis-(diphenylphosphinoferrocene)palladium dichloride dichloromethane complex (Pd(dppf)₂Cl₂).

In another particular aspect of the embodiment, and in combination with any other particular aspects not inconsistent, the base in step (a) is selected from the group consisting of diisopropyl ethylamine, lithium carbonate, dicyclohexyl methylamine and triethylamine. Preferably, the base in step (a) is diisopropyl ethylamine.

In another embodiment, and in combination with any other embodiments not inconsistent, the invention provides a method of preparing the compound of formula Id Id

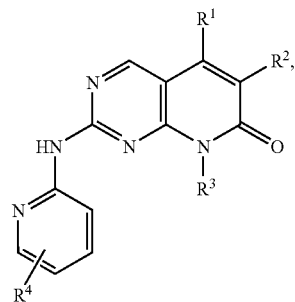

comprising the steps of (c) halogenating a compound of formula Ic

Ic

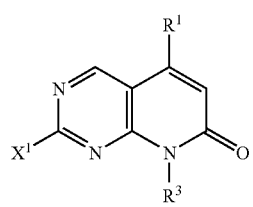

under a halogenation condition, to give a compound of formula Ic1

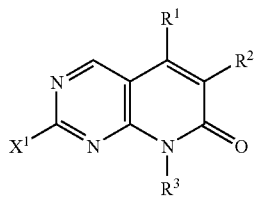

wherein X¹ is halogen, sulfide, sulfoxide or sulfone; and subsequently (d) reacting the compound of formula Ic1 with a compound of formula Ic3

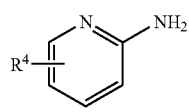

in the presence of a lithium base and in a suitable solvent, to give the compound of formula Id.

In one particular aspect of the embodiment, and in combination with any other particular aspects not inconsistent, the halogenation condition in step (c) is $(R^2)_2$ in the presence of acetic acid, potassium acetate or sodium acetate.

In another particular aspect of the embodiment, and in combination with any other particular aspects not inconsistent, the lithium base is lithium bis(trimethylsilyl)amide.

In another particular aspect of the embodiment, and in combination with any other particular aspects not inconsistent, X¹ is Cl.

In another embodiment, and in combination with any other embodiments not inconsistent, the invention provides another method of preparing the compound of formula Id

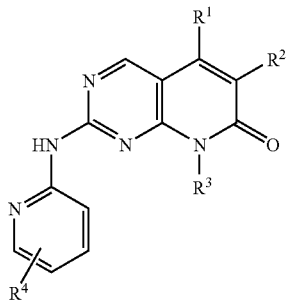

comprising the steps of
(e) reacting a compound of formula Ic

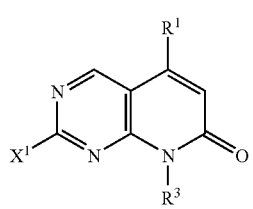

with a compound of formula Ic3

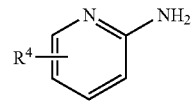

in the presence of a lithium base, and in a suitable solvent to give a compound of Ic2

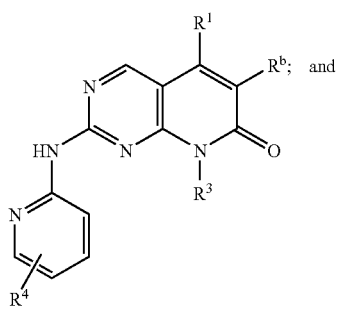

(f) halogenating the compound of formula Ic2 under a halogenation condition to give the compound of formula Id.

In one particular aspect of the embodiment, and in combination with any other particular aspects not inconsistent, the halogenation condition in step (f) is $(R^2)_2$ in the presence of acetic acid, potassium acetate or sodium acetate.

In another particular aspect of the embodiment, and in combination with any other particular aspects not inconsistent, the lithium base in step (e) is lithium bis(trimethylsilyl)amide.

In another particular aspect of the embodiment, and in combination with any other particular aspects not inconsistent, X¹ is Cl.

In another embodiment, and in combination with any other embodiments not inconsistent, the invention provides a method of preparing the compound of formula Ic

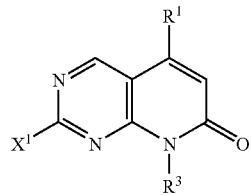

comprising the steps of
(g) reacting a compound of formula Ib:

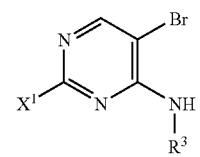

with a compound of the formula

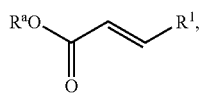

wherein $R^a$ is selected from H, $C_1$-$C_3$alkyl and —C(O)—$C_1$-$C_3$alkyl, in the presence of a base, a transition metal catalyst and optionally a phosphine agent, and in a suitable solvent; and (h) a intramolecular cyclization reaction of the resulting product of step (g) to give the compound of formula Ic.

In one particular aspect of this embodiment, and in combination with any other particular aspects not inconsistent, the transition metal catalyst in step (g) is a palladium compound selected from the group consisting of tetrakis(triphenylphosphine)palladium [($Ph_3P$)$_4$Pd], tris(dibenzylideneacetone)dipalladium [$Pd_2(dba)_3$], bis(dibenzylideneacetone) palladium (0) [$(dba)_2$Pd], palladium acetate [Pd(OAc)$_2$], palladium chloride (PdCl$_2$), bis(benzonitrile)dichloropalladium [($C_6H_5$CN)$_2$PdCl$_2$] and (Bis-(diphenylphosphinoferrocene) palladium dichloride dichloromethane complex (Pd(dppf)$_2$Cl$_2$), and the phospine compound is selected from 2,2'-bis(diphenylphosphino)-1,1'-binaphthalene (BINAP), 1,3 bis (diphenylphosphino)propane, triphenylphosphine (Ph$_3$P), triorthotolylphosphine [(o-CH$_3$Ph)$_3$P] and tri-t-butylphosphine. Preferably, the transitional metal catalyst is in step (g) is palladium dichloride dibenzonitrile and step (g) is carried out in the presence of triorthotolylphosphine.

In another particular aspect of this embodiment, and in combination with any other particular aspects not inconsistent, the base in step (g) is diisopropylethylamine and the transition metal catalyst in step (g) is palladium dichloride dibenzonitrile and step (g) is carried out in the presence of triorthotolylphosphine.

In another particular aspect of this embodiment, and in combination with any other particular aspects not inconsistent, $R^a$ is H and the intramolecular cyclization in step (h) is carried out in the presence of a coupling agent. Typical such coupling agents can be carbodiimides such as N,N'-dicyclohexylcarbodiimide (DCC), N,N'-di-tert-butylcarbodiimide and N,N'-diisopropylcarbodiimide; carbonyldiimidazole derivatives such as 1,1'-carbonyldiimidazole (CDI), 1,1'-carbonyl-di-(1,2,4-triazole) and 1,1'-thiocarbonyldiimidazole; active ester formation reagent such as N-hydroxysuccinimide, N,N'-disuccinimidyl carbonate and 2-thiazoline-2-thiol; and other reagents such as 1,3-Dimethyl-3,4,5,6-tetrahydro-2(1H)-pyrimidinone, acetic anhydride, trifluoromethanesulfonic anhydride and acetic chloride.

In another particular aspect of this embodiment, and in combination with any other particular aspects not inconsistent, $R^a$ is H and the intramolecular cyclization in step (h) is carried out in the presence of acetic anhydride or acetic chloride.

In another particular aspect of this embodiment, and in combination with any other particular aspects not inconsistent, solvent of step (g) is selected from toluene and THF.

In another embodiment, and in combination with any other embodiment not inconsistent, the invention provides a method of preparing the compound of formula Ib

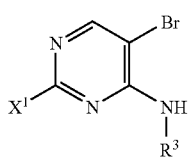

comprising the step of
(i) reacting a compound of formula Ia

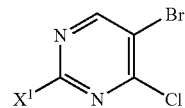

with a compound of the formula $R^3$—$NH_2$ in the presence of a base and in a suitable solvent to give the compound of formula Ib.

This invention identifies 2-(2'-pyridyl)pyrido[2,3-d]pyrimidinones as compounds that are useful for treating uncontrolled cell proliferative diseases, including, but not limited to, proliferative diseases such as cancer, restenosis and rheumatoid arthritis. In addition, these compounds are useful for treating inflammation and inflammatory diseases. In addition, these compounds have utility as antiinfective agents. Moreover, these compounds have utility as chemoprotective agents through their ability to inhibit the cell cycle progression of normal untransformed cells. Many of the compounds of the invention display unexpected improvements in selectivity for the serine/threonine kinases cyclin-dependent kinase 4 and cyclin-dependent kinase 6. The compounds are readily synthesized and can be administered to patients by a variety of methods.

Compounds of formula I may contain chiral centers and therefore may exist in different enantiomeric and diastereomeric forms. This invention relates to all optical isomers and all stereoisomers of compounds of the formula I, both as racemic mixtures and as individual enantiomers and diastereoisomers of such compounds, and mixtures thereof, and to all pharmaceutical compositions and methods of treatment defined above that contain or employ them, respectively.

As the compounds of formula I of this invention may possess at least two asymmetric centers, they are capable of occurring in various stereoisomeric forms or configurations. Hence, the compounds can exist in separated (+)- and (−)-optically active forms, as well as mixtures thereof. The present invention includes all such forms within its scope. Individual isomers can be obtained by known methods, such as optical resolution, optically selective reaction, or chromatographic separation in the preparation of the final product or its intermediate.

The compounds of the present invention can exist in unsolvated forms as well as solvated forms, including hydrated forms. In general, the solvated forms, including hydrated forms, are equivalent to unsolvated forms and are intended to be encompassed within the scope of the present invention.

The present invention also includes isotopically labelled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^2H$, $^3H$, $^{13}C$, $^{11}C$, $^{14}C$, $^{15}N$, $^{18}O$, $^{17}O$, $^{31}P$, $^{32}P$, $^{35}S$, $^{18}F$, and $^{36}C$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labelled compounds of the present invention, for example those into which radioactive isotopes such as $^3H$ and $^{14}C$ are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically labelled compounds of formula I of this invention and prodrugs thereof can generally be prepared by carrying out the procedures disclosed in the Schemes and/or in the Examples and Preparations below, by substituting a readily available isotopically labelled reagent for a non-isotopically labelled reagent.

The compounds of Formula I are capable of further forming pharmaceutically acceptable formulations comprising salts, including but not limited to acid addition and/or base salts, solvents and N-oxides of a compound of Formula I.

This invention also provides pharmaceutical formulations comprising a therapeutically effective amount of a compound of Formula I or a therapeutically acceptable salt thereof and a pharmaceutically acceptable carrier, diluent, or excipient therefor. All of these forms are within the present invention.

By "alkyl," in the present invention is meant a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, iso-pentyl, n-hexyl, and the like.

"Alkenyl" means straight and branched hydrocarbon radicals having from 2 to 8 carbon atoms and at least one double bond and includes, but is not limited to, ethenyl, 3-buten-1-yl, 2-ethenylbutyl, 3-hexen-1-yl, and the like. The term "alkenyl" includes, cycloalkenyl, and heteroalkenyl in which 1 to 3 heteroatoms selected from O, S, N or substituted nitrogen may replace carbon atoms.

"Alkynyl" means straight and branched hydrocarbon radicals having from 2 to 8 carbon atoms and at least one triple bond and includes, but is not limited to, ethynyl, 3-butyn-1-yl, propynyl, 2-butyn-1-yl, 3-pentyn-1-yl, and the like.

"Cycloalkyl" means a monocyclic or polycyclic hydrocarbyl group having from 3 to 8 carbon atoms, for instance, cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, amino, alkyl, and dialkylamino, and the like. Also included are rings in which 1 to 3 heteroatoms replace carbons. Such groups are termed "heterocyclyl," which means a cycloalkyl group also bearing at least one heteroatom selected from O, S, N or substituted nitrogen. Examples of such groups include, but are not limited to, oxiranyl, pyrrolidinyl, piperidyl, tetrahydropyran, and morpholine.

By "alkoxy," is meant straight or branched chain alkyl groups having 1-10 carbon atoms and linked through oxygen. Examples of such groups include, but are not limited to, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, and 3-methylpentoxy. In addition, alkoxy refers to polyethers such as —O—(CH$_2$)$_2$—O—CH$_3$, and the like.

"Acyl" means an alkyl or aryl (Ar) group having from 1-10 carbon atoms bonded through a carbonyl group, i.e., R—C(O)—. For example, acyl includes, but is not limited to, a C$_1$-C$_6$ alkanoyl, including substituted alkanoyl, wherein the alkyl portion can be substituted by NR$^4$R$^5$ or a carboxylic or heterocyclic group. Typical acyl groups include acetyl, benzoyl, and the like. Similarly the term "acetyl" refers to the formula —C(O)CH$_3$.

The alkyl, alkenyl, alkoxy, and alkynyl groups described above are optionally substituted, preferably by 1 to 3 groups selected from NR$^4$R$^5$, phenyl, substituted phenyl, thio C$_1$-C$_6$ alkyl, C$_1$-C$_6$ alkoxy, hydroxy, carboxy, C$_1$-C$_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing C$_1$-C$_6$ alkyl or (CH$_2$)$_p$Ph where p is 1, 2, or 3. Perhalo and polyhalo substitution is also included.

Examples of substituted alkyl groups include, but are not limited to, 2-aminoethyl, 2-hydroxyethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include, but are not limited to, 2-methoxyethynyl, 2-ethylsulfanylethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include, but are not limited to, dimethylaminomethyl, carboxymethyl, 4-dimethylamino-3-buten-1-yl, 5-ethylmethylamino-3-pentyn-1-yl, 4-morpholinobutyl, 4-tetrahydropyrimidylbutyl, 3-imidazolidin-1-ylpropyl, 4-tetrahydrothiazol-3-yl-butyl, phenylmethyl, 3-chlorophenylmethyl, and the like.

The term "anion" means a negatively charged counterion such as chloride, bromide, trifluoroacetate, and triethylammonium.

By the term "halogen" in the present invention is meant fluorine, bromine, chlorine, and iodine.

By "heteroaryl" is meant one or more aromatic ring systems of 5-, 6-, or 7-membered rings containing at least one and up to four heteroatoms selected from nitrogen, oxygen, or sulfur. Such heteroaryl groups include, for example, thienyl, furanyl, thiazolyl, triazolyl, imidazolyl, (is)oxazolyl, oxadiazolyl, tetrazolyl, pyridyl, thiadiazolyl, oxadiazolyl, oxathiadiazolyl, thiatriazolyl, pyrimidinyl, (iso)quinolinyl, napthyridinyl, phthalimidyl, benzimidazolyl, and benzoxazolyl. A preferred heteroaryl is pyridine.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl, anthryl, or phenanthryl), which can be mono-, di-, or trisubstituted with, e.g., halogen, lower alkyl, lower alkoxy, lower alkylthio, trifluoromethyl, lower acyloxy, aryl, heteroaryl, and hydroxy. A preferred aryl is phenyl.

The term "sulfide" refers to moieties of the formula —S—R. The term "sulfoxide" refer to the moieties of the formula —S(O)—R and the term "sulfone" refers to moieties of the formula —S(O)$_2$—R. R in this definition is typically a lower alkyl C$_1$-C$_6$ alkyl.

In addition, the following abbreviations as used throughout the Examples are defined herein: "Et" means ethyl, "Bu" means butyl, "Boc" means tert-butyloxycarbonyl, "AcOH" means sodium acetate, "AcOK" means potassium acetate, "PD" means palladium, "IPA" means isopropanol, "THF" means tetrahydrofuran, "MTBE" means methyl tert butyl ether; "NBS" means N-bromosuccinimide, "DBU" means 1,8 diazabicyclo[5.4.0]undec-7-ene, "DBN" means 1,5-diazabicyclo[4.3.0]non-5-ene, "LHMDS" means lithium bis(trimethylsilyl)amide.

The term "cancer" includes, but is not limited to, the following cancers: cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia.

The term "treating", as used herein, refers to reversing, alleviating, inhibiting the progress of, or preventing the disorder or condition to which such term applies, or preventing one or more symptoms of such condition or disorder. The term "treatment", as used herein, refers to the act of treating, as "treating" is defined immediately above.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention.

The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. In so far as the compounds of formula I of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine; see, for example, Berge et al., supra.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

Salts may be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts may also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts may include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. (See, for example, Berge S. M. et al., "Pharmaceutical Salts," *J. Pharm. Sci.*, 1977; 66:1-19 which is incorporated herein by reference.) Examples of pharmaceutically acceptable, non-toxic esters of the compounds of this invention include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds of the present invention may be prepared according to conventional methods "March's Advanced Organic Chemistry, $5^{th}$ Edition". M. B. Smith & J. March, John Wiley & Sons, 2001.

Examples of pharmaceutically acceptable, non-toxic amides of the compounds of this invention include amides derived from ammonia, primary $C_1$-$C_6$ alkyl amines and secondary $C_1$-$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds of the invention may be prepared according to conventional methods such as "March's Advanced Organic Chemistry, $5^{th}$ Edition". M. B. Smith & J. March, John Wiley & Sons, 2001.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in *Bioreversible Carriers in Drug Design*, ed. Edward B. Roche, American Pharmaceutical Association and Pergamon Press, 1987, both of which are hereby incorporated by reference.

This invention provides a method of treating a disorder or condition selected from the group consisting of cell proliferative disorders, such as cancer, vascular smooth muscle proliferation associated with atherosclerosis, postsurgical vascular stenosis, restenosis, and endometriosis; infections, including viral infections such as DNA viruses like herpes and RNA viruses like HIV, and fungal infections; autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease, in a mammal, including human, comprising administering to said mammal an amount of a compound of formula I, or a pharmaceutically acceptable salt thereof, that is effective in treating such disorder or condition This invention further provides compounds of formula I that are useful for treating abnormal cell proliferation such a cancer. The invention provides a method of o treating the abnormal cell proliferation disorders such as a cancer selected from the group consisting of cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia, comprising administering a therapeutically effective amount of a compound of formula I, or a pharmaceutically acceptable salt thereof, to a subject in need of such treatment.

A further embodiment of this invention is a method of treating subjects suffering from diseases caused by vascular smooth muscle cell proliferation. Compounds within the scope of the present invention effectively inhibit vascular smooth muscle cell proliferation and migration. The method comprises administering to a subject in need of treatment an amount of a compound of formula I, or a pharmaceutically acceptable salt thereof, sufficient to inhibit vascular smooth muscle proliferation, and/or migration.

This invention further provides a method of treating a subject suffering from gout comprising administering to said subject in need of treatment an amount of a compound of formula I, or a pharmaceutically acceptable salt thereof, sufficient to treat the condition.

This invention further provides a method of treating a subject suffering from kidney disease, such as polycystic kidney disease, comprising administering to said subject in need of treatment an amount of a compound of formula I, or a pharmaceutically acceptable salt thereof, sufficient to treat the condition.

Because of their inhibitory activity against cdks and other kinases, the compounds of the present invention are also useful research tools for studying the mechanism of action of those kinases, both in vitro and in vivo.

The above-identified methods of treatment are preferably carried out by administering a therapeutically effective amount of a compound of Formula I (set forth below) to a subject in need of treatment. Compounds of the present invention are substituted 2-aminopyridines that are potent inhibitors of cyclin-dependent kinases 4 (cdk4). The compounds are readily synthesized and can be administered by a variety of routes, including orally and parenterally, and have little or no toxicity. The compounds of the invention are members of the class of compounds of Formula I.

This invention provides a pharmaceutical composition comprising a therapeutically effective amount of a compound of the formula I, or a pharmaceutically acceptable salt thereof, and a pharmaceutically acceptable carrier, diluent, or excipient therefor.

Many of the compounds of the present invention are selective inhibitors of cyclin dependent kinase cdk4, which is to say that they inhibit cdk4 more potently than they inhibit tyrosine kinases and other serine-threonine kinases including other cyclin-dependent kinases such as cdk2. Despite their selectivity for cdk4 inhibition, compounds of the invention may inhibit other kinases, albeit at higher concentrations than those at which they inhibit cdk4. However, compounds of the present invention also may inhibit Cdk6 at similar concentrations to those necessary for inhibition of cdk4 since cdk6 is structurally similar to and performs similar functions to cdk4.

Preferred embodiments of the present invention are compounds of the formula I inhibit cdk4 at least about 100-fold more potently than they inhibit cdk2.

A preferred embodiment of the present invention provides a method of inhibiting cdk4 at a lower dose than is necessary to inhibit cdk2 comprising administration of a preferred compound of formula I in an amount that selectively inhibits cdk4 over cdk2.

The compounds of formula I of this invention have useful pharmaceutical and medicinal properties. Many of the compounds of formula I of this invention exhibit significant selective cdk4 inhibitory activity and therefore are of value in the treatment of a wide variety of clinical conditions in which cdk4 kinase is abnormally elevated, or activated or present in normal amounts and activities, but where inhibition of the cdks is desirable to treat a cellular proliferative disorder. Such disorders include, but are not limited to those enumerated in the paragraphs below.

The compounds of the present invention are useful for treating cancer (for example, leukemia and cancer of the lung, breast, prostate, and skin such as melanoma) and other proliferative diseases including but not limited to psoriasis, HSV, HIV, restenosis, and atherosclerosis. To utilize a compound of the present invention to treat cancer, a patient in need of such treatment, such as one having cancer or another proliferative disease, is administered a therapeutically effective amount of a pharmaceutically acceptable composition comprising at least one compound of the present invention.

Compounds of the present invention are selective inhibitors of cdk4, which is to say that they inhibit cdk4 more potently than they inhibit tyrosine kinases and other serine-threonine kinases including other cyclin-dependent kinases such as cdk2. Despite their selectivity for cdk4 inhibition, compounds of the invention may inhibit other kinases, albeit at higher concentrations than those at which they inhibit cdk4. However, compounds of the present invention also may inhibit cdk6 at similar concentrations to those necessary for inhibition of cdk4 since cdk6 is structurally similar to and performs similar functions to cdk4.

DETAILED DESCRIPTION OF THE INVENTION

An illustration of the preparation of compounds of the present invention is shown in Schemes 1 to 2.

The compounds of the invention may be prepared according to the general Scheme I. Unless otherwise designated, the $R^1$, $R^2$, $R^3$, $R^4$, $R^5$, $R^6$, $X^1$, $R^a$ and $R^b$ are as defined above.

Scheme I
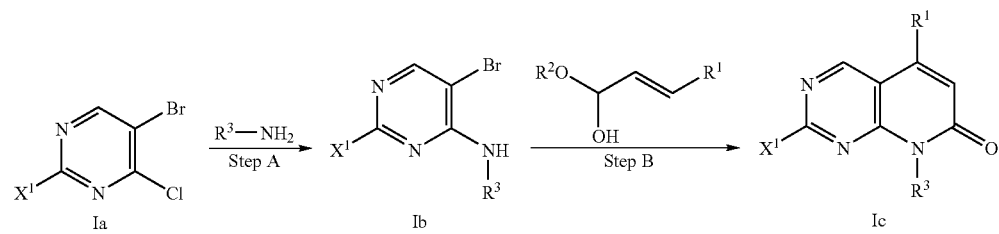
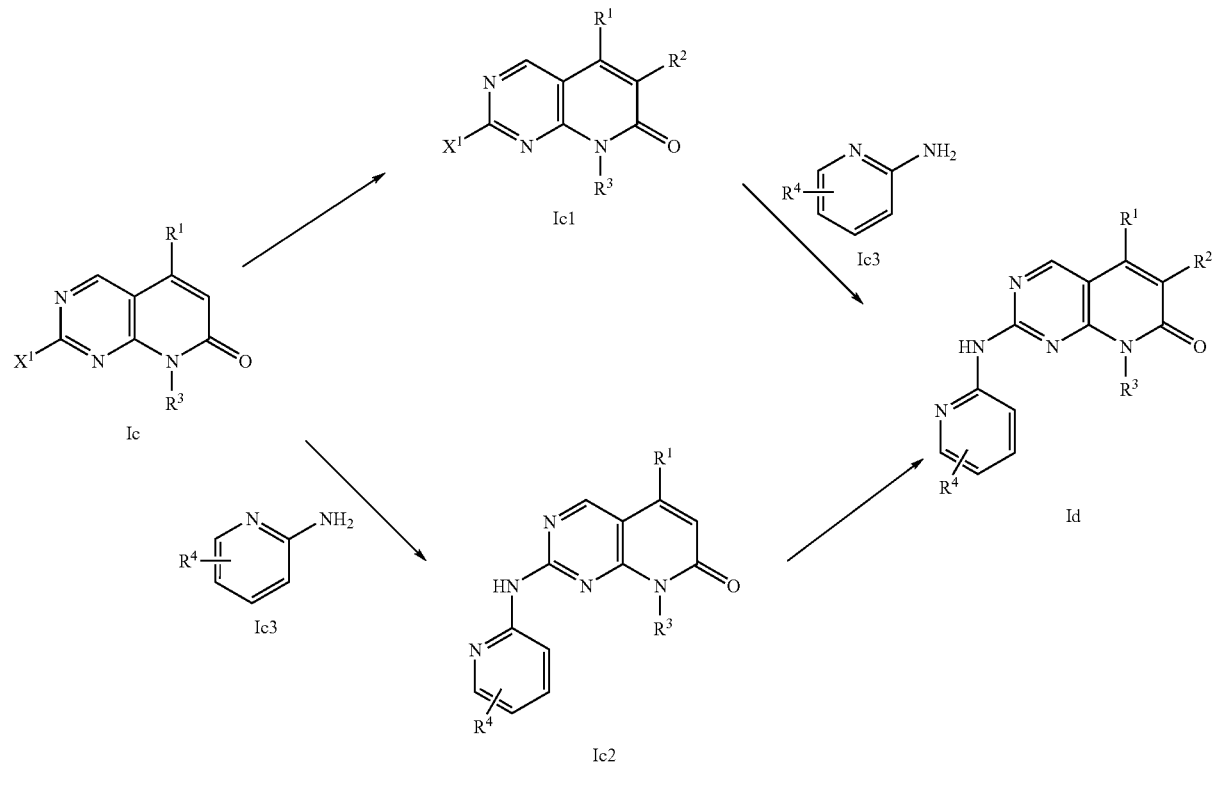
Scheme II
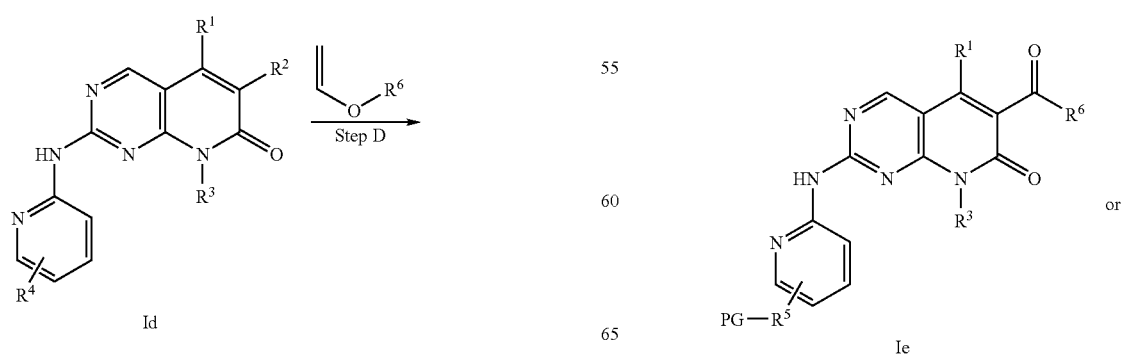

19

-continued

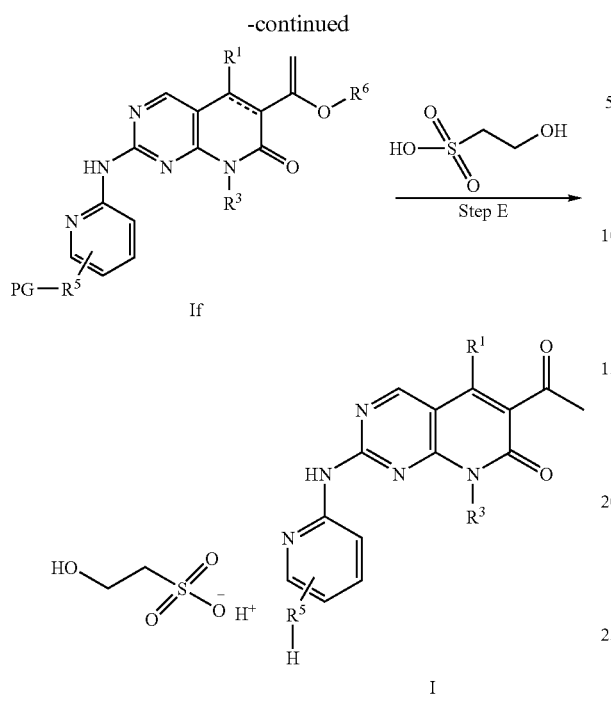

Step A: Amination

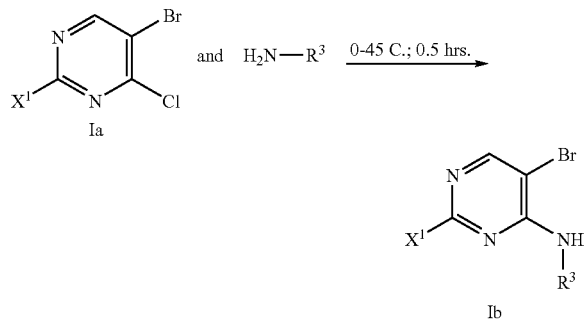

The assembly of compound Ib generally starts with the addition of a substituted amine to 5-bromo 2,4-dihalopyrimidine Ia at a temperature range of about 0° to about 45° for a duration of at least about 0.5 hours in a suitable solvent such as ethanol. Alternative solvents to ethanol would include acetonitrile, toluene, THF or MTBE and combinations thereof. In Example 3 below, the substituted amine is a cyclopentyl amine and the reaction proceeds at about 25° C. for about 2 hours. The addition is regioselective, giving greater than 9:1 ratio of the desired to undesired isomer. Crystallization may then be performed to remove the undesired isomer from the product. The Ib intermediate can also be made in a two-step procedure starting from the less expensive 2,4-dichloropyrimidine. This reaction is also regioselective although less so, giving a 3:1 ratio of desired to undesired isomer. The desired isomer may be separated from the undesired isomer by an acidic extraction, and the correct isomer can be brominated in high yield to produce the desired product Ib, i.e. 5-bromo2-chloro-4-cyclopentylamino pyrimidine.

20

Step B: Heck Coupling and Subsequent Cyclization

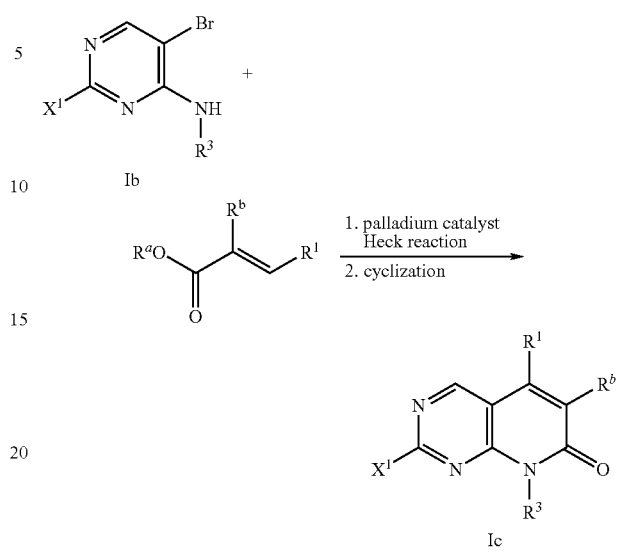

The Heck coupling and subsequent cyclization to form compound Ic generally proceeds by mixture of compound Ib with an substituted olefin in the presence of a transition metal catalyst, usually a palladium (0) or palladium (II) catalyst, a base and optionally in the presence of a phosphine agent. Typical palladium(0) catalyst includes tetrakis(triphenylphosphine)palladium [(Ph$_3$P)$_4$Pd], tris(dibenzylideneacetone)dipalladium [Pd$_2$(dba)$_3$] and bis(dibenzylideneacetone) palladium(0) [(dba)$_2$Pd]. Typical palladium(II) compound includes palladium acetate [Pd(OAc)$_2$], palladium chloride (PdCl$_2$), bis(benzonitrile)dichloropalladium [(C$_6$H$_5$CN)$_2$PdCl$_2$] and (Bis-(diphenylphosphinoferrocene) palladium dichloride dichloromethane complex (Pd(dppf)$_2$Cl$_2$). Typical phospine compound used in the Heck coupling includes monodentate phosphine agents such as triphenylphosphine (Ph$_3$P), triorthotolylphosphine [(o-CH$_3$Ph)$_3$P], tri-t-butylphosphine and bidentate phosphine agents such as 2,2'-bis(diphenylphosphineo)-1,1'-binaphthyl (BINAP) and 1,3 bis(diphenylphosphino)propane. A preferred condition of the current invention is to use palladium dichloride dibenzonitrile in combination with triorthotolylphosphine. Typical base that can be used in Heck reaction includes diisopropyl ethylamine (DIEA), triethyl amine (TEA), lithium carbonate and dicyclohexyl methylamine. A preferred amine is DIEA. The Heck reaction is carried out at about 60° C. to about 90° C. for at least 10 hours. In Example 3, the solvent used was THF and the base was diisopropylethylamine and the solution was heated to about 70° C. for at least 16 hours. Alternative solvents include toluene, THF and combinations thereof. The intermediate ester or acid thus formed is cyclized by heating, by treating with an alkoxide base such as lithium, sodium, or potassium ethoxide, a strong amine base such as 1,8-diazabicyclo[5.4.0]undec-7ene (DBU) or 1,5-diazabicyclo[4.3.0]non-5-ene (DBN), or preferably, when R$^a$ is H, by the addition of a dehydrating agent such as acetic anhydride, acetyl chloride or phosphorus oxy chloride. R$^b$ in the above reaction may be H or C$_1$-C$_3$alkyl and is typically carried forward in Ic. For the preferred compounds of the invention however, R$^b$ is H.

Step C: Amino-pyridinyl Coupling

Progression to compound Id includes two steps.

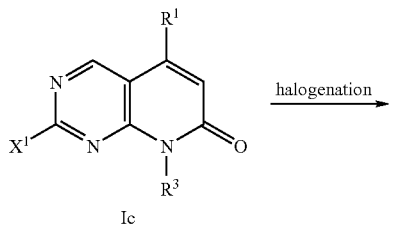

Ic halogenation →

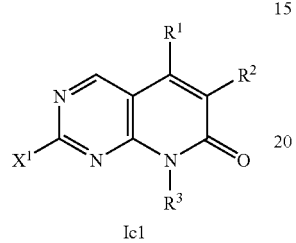

Ic1

Halogenation of compound Ic or Ic2 can be done under many halogenation conditions. Preferably, it is carried out by the addition of $Br_2$ or $I_2$ and a base in a suitable solvent and heating to about 40° C. to about 60° C. and stirring for at least 16 hours. In Example 4a below, the base was sodium acetate and the solvent was acetic acid and the solution was heated to about 50° C. and stirred for about 35 hours. Alternative bases include potassium acetate and alternative solvents include methanol and dichloromethane and combinations thereof. Preferred halogenating agents include bromine, NBS or dibromohydantoin.

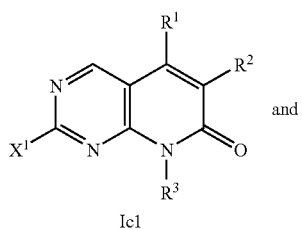

Ic1 and

-continued

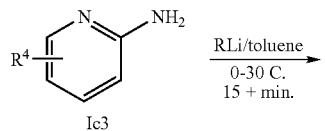

Ic3

$\xrightarrow{\text{RLi/toluene}}_{\substack{0\text{-}30\text{ C.}\\15+\text{ min.}}}$

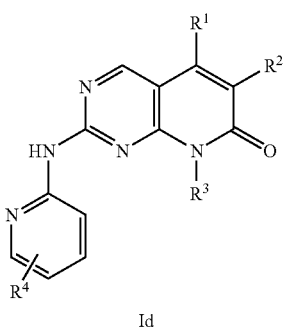

Id

Joinder of the aminopyridinyl side chain Ic3 to the intermediate Ic or Ic1 proceeds by adding the aminopyridinyl side chain Ic3 with a lithium base and toluene in a suitable solvent. The aminopyridinyl side chain Ic3 is preferably prepared separately by first mixing with toluene and the lithium base in a suitable solvent. Compound Ic or Ic1 is preferably separately slurried in toluene prior to combining with the amine Ic3 mixture. The reaction is allowed to proceed at 0 to 30° C. for at least 15 minutes prior to quenching. The preferred temperature is 20° C. for at least 30 minutes prior to quenching. In Example 4 below, the lithium base was lithium bis(trimethylsilyl)amide but any lithium base can be used as an alternative. Other suitable solvents include MTBE and less preferably THF.

As defined previously, $R^4$ is $R^5$—PG and PG is an amine protecting group. In example 4 below, $R^4$ is Boc, but $R^4$ may be other acid-labile amine protecting group such as hexadienyloxycarbonyl (Hdoc), Trityl, and trityl derivatives such as 9-(9-phenylfluorenyl) or methoxytrityl and dimethoxytrityl.

Step D: Regioselective Heck Coupling

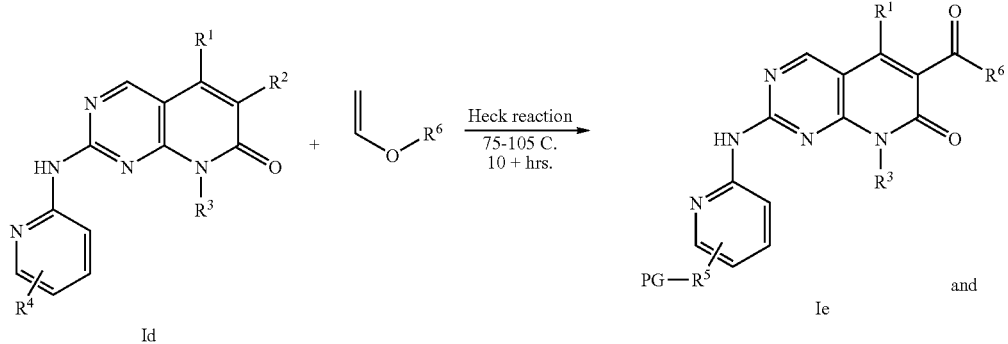

-continued

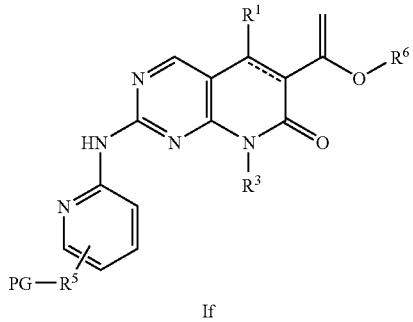

If

Compounds of formula Id are mixed with a vinyl ether, and a base in a suitable solvent such as n-butanol. A palladium catalyst is then added and the mixture heated to a range of about 75° C. to about 105° C. for at least 10 hours. In Example 5 below, the mixture was stirred at 95° C. for 20 hrs in n-butanol. Preferred catalysts include those listed in Step B of this section. More preferable catalysts are palladium having bidentate ligands and the most preferred catalyst is Bis-(diphenylphosphinoferrocene)palladium dichloride dichloromethane complex [Pd(dppf)$_2$Cl$_2$]. Alternative bidentate ligands on the palladium catalyst include Binap and 1,3 Bis (diphenylphosphino) and alternative solvents include DMF (N,N-dimethyl foramide) and DMI (N,N-dimethyl imidazolidinone). A preferred base is diisopropyl ethylamine (DIEA). Alternate bases include lithium carbonate (the presence of lithium carbonate increases the selectivity of the reaction), dicyclohexyl methylamine, triethylamine. Preferred vinyl ethers are n-butyl vinyl either and ethyl vinyl either.

Step E: Deprotection and addition of Isethionic Acid

The final step to the isethionate salt includes heating compounds Ie or If to about 55-60° C. and adding isethionic acid using methods as shown in WO2005005426. The reaction occurs over at least 1.5 hours and more preferably 3 hours.

The aminopyridinyl compound of formula Ic3 of Scheme I can be prepared from commercially available 5-bromo-2-nitropyridine by base or palladium promoted displacement of the bromine by a nucleophile such as an alcohol or a primary or secondary amine, followed by reduction of the nitro group. A representative example of this method is illustrated in Scheme III below and a specific example is disclosed in Example 2 below. Examples of bases that may be used for this reaction include K$_2$CO$_3$ or Na$_2$CO$_3$. These bases may be used in the presence of a phase transfer catalyst such as Bu$_4$NI. Palladium promoted reactions are typically performed with catalysts such as Pd(OAc)$_2$ (Palladium(II) Acetate), Pd$_2$(dba)$_3$, Pd(dba)$_2$ (bis(dibenzylideneacetone)palladium) or Pd(PPh$_3$)$_4$(tetrakis(triphenylphosphine)palladium) and the like in nonpolar organic solvents such as DMSO, triethy-

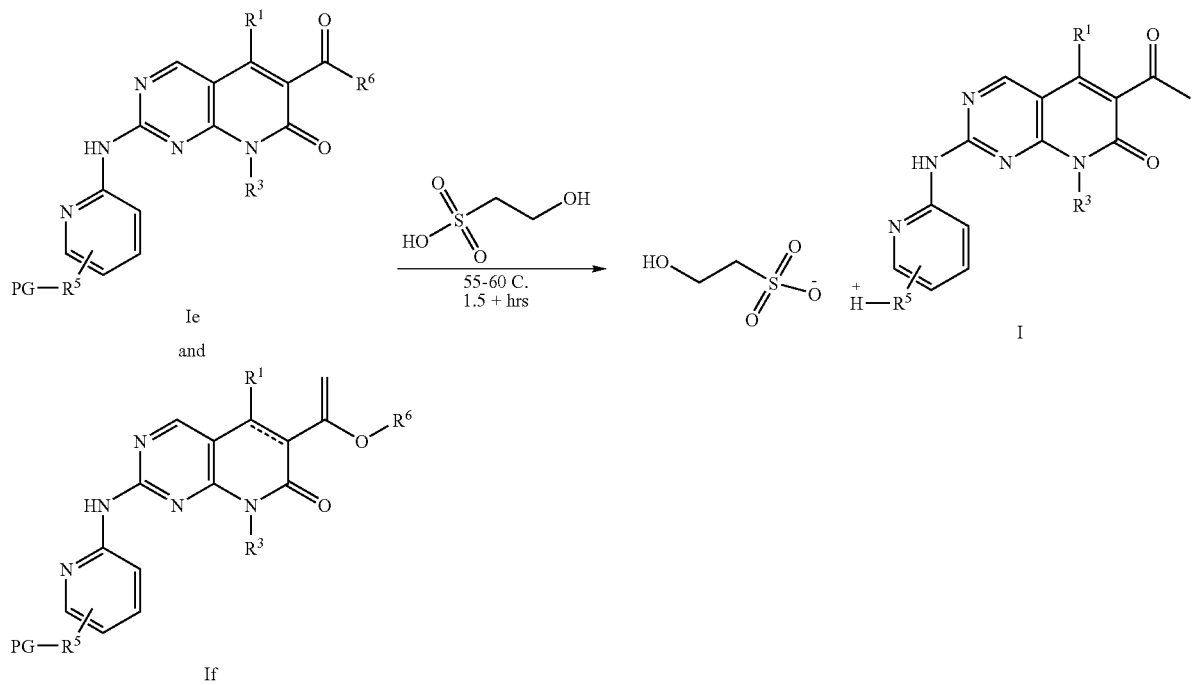

lamine, DMF, IPA/H₂O, Butanol/H₂O, DMI, benzene, toluene, tetrahydrofuran or acetonitrile at temperatures from 25-110° C. These catalysts are typically employed with a suitable ligand such as BINAP (2,2'-Bis(diphenylphosphino)-1,1'-binaphthalene), Xantphos® (Strem Chemicals Inc.) or a related phosphine-based Pd ligand. Reduction of the nitro group is typically performed using Raney Nickel although other reducing agents also may be used including palladium on charcoal or Fe/HCl.

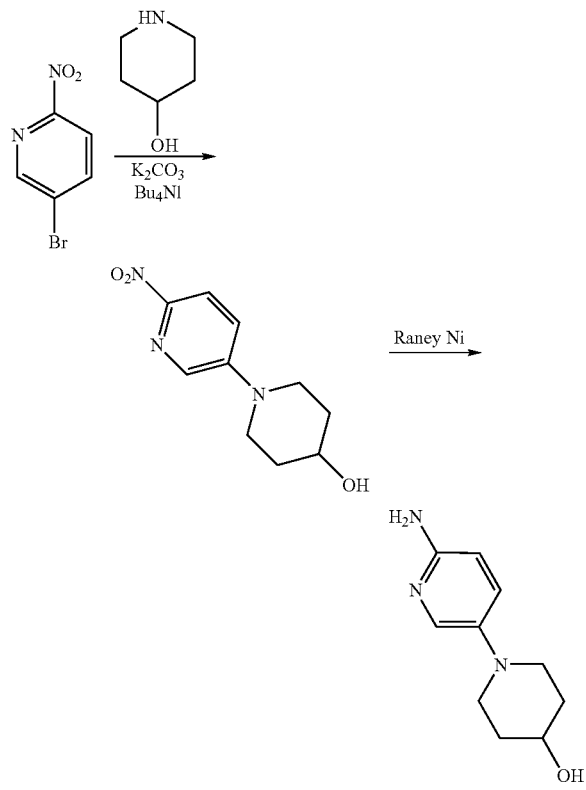

Further substituted pyridine derivatives Ic3 of Scheme I can be prepared by methods known to those in the art. Examples of representative procedures may be found in Comprehensive Heterocyclic Chemistry, Eds. A. R. Katritzky, C. W. Rees, 1984, Pergamon, NY; Volume 2, Chapter 2.08, *Pyridines and their Benzoderivatives: Synthesis*, Gurnos Jones. Also, refer to Comprehensive Heterocyclic Chemistry II, Eds. A. R. Katritzky, C. W. Rees., E. Scriven, 1996, Pergamon, NY; Volume 25, Chapter 5.05, *Pyridines and their Benzoderivatives: Synthesis*, Gurnos Jones. Representative examples are illustrated in Scheme IV below.

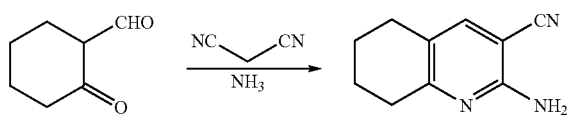

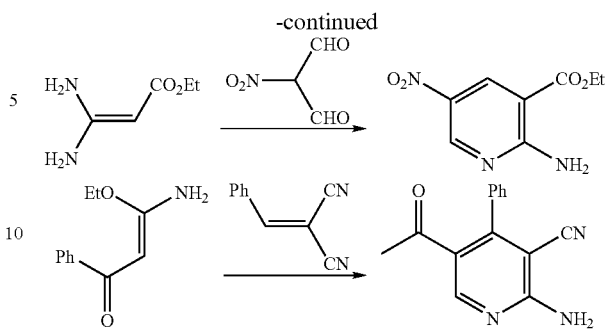

The compounds of the present invention can be formulated and administered in a wide variety of oral and parenteral dosage forms, including transdermal and rectal administration. It will be recognized to those skilled in the art that the following dosage forms may comprise as the active component, either a compound of Formula I or a corresponding pharmaceutically acceptable salt or solvate of a compound of Formula I.

This invention also comprises a pharmaceutical formulation comprising a therapeutically effective amount of a compound of Formula I together with a pharmaceutically acceptable carrier, diluent, or excipient therefor. For preparing pharmaceutical compositions with the compounds of the present invention, pharmaceutically acceptable carriers can be either a solid or liquid. Solid form preparations include powders, tablets, pills, capsules, cachets, suppositories, and dispensable granules. A solid carrier can be one or more substances which may also act as diluents, flavoring agents, binders, preservatives, tablet disintegrating agents, or an encapsulating material.

In powders, the carrier is a finely divided solid such as talc or starch which is in a mixture with the finely divided active component. In tablets, the active component is mixed with the carrier having the necessary binding properties in suitable proportions and compacted in the shape and size desired.

The formulations of this invention preferably contain from about 5% to about 70% or more of the active compound. Suitable carriers include magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. A preferred form for oral use are capsules, which include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient size molds, allowed to cool, and thereby to solidify.

Liquid form preparations include solutions, suspensions, and emulsions such as water or water/propylene glycol solutions. For parenteral injection, liquid preparations can be formulated in solution in aqueous polyethylene glycol solution, isotonic saline, 5% aqueous glucose, and the like. Aqueous solutions suitable for oral use can be prepared by dissolving the active component in water and adding suitable colorants, flavors, stabilizing and thickening agents as desired. Aqueous suspensions suitable for oral use can be made by dispersing the finely divided active component in water and mixing with a viscous material, such as natural or synthetic gums, resins, methylcellulose, sodium carboxymethylcellulose, or other well-known suspending agents.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like. Waxes, polymers, microparticles, and the like can be utilized to prepare sustained-release dosage forms. Also, osmotic pumps can be employed to deliver the active compound uniformly over a prolonged period.

The pharmaceutical preparations of the invention are preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The therapeutically effective dose of a compound of Formula I will vary from approximately 0.01 mg/kg to approximately 100 mg/kg of body weight per day. Typical adult doses will be approximately 0.1 mg to approximately 3000 mg per day. The quantity of active component in a unit dose preparation may be varied or adjusted from approximately 0.1 mg to approximately 500 mg, preferably about 0.6 mg to 100 mg according to the particular application and the potency of the active component. The composition can, if desired, also contain other compatible therapeutic agents. A subject in need of treatment with a compound of Formula I is administered a dosage of about 0.6 to about 500 mg per day, either singly or in multiple doses over a 24-hour period. Such treatment may be repeated at successive intervals for as long as necessary.

This invention provides a pharmaceutical composition for treating a disorder or condition selected from the group consisting of cell proliferative disorders, such as cancer, vascular smooth muscle proliferation associated with atherosclerosis, postsurgical vascular stenosis, restenosis, and endometriosis; infections, including viral infections such as DNA viruses like herpes and RNA viruses like HIV, and fungal infections; autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease.

The examples presented below are intended to illustrate particular embodiments of the invention, and are not intended to limit the scope of the specification or the claims in any way.

Those having skill in the art will recognize that the starting materials may be varied and additional steps employed to produce compounds encompassed by the present invention, as demonstrated by the following examples. The following examples are for illustrative purposes only and are not intended, nor should they be construed as limiting the invention in any manner. Those skilled in the art will appreciate that variations and modifications can be made without violating the spirit or scope of the invention.

The invention and the manner and process of making and using it, are now described in such full, clear, concise, and exact terms as to enable any person skilled in the art to which it pertains, to make and use the same. It is to be understood that the foregoing describes preferred embodiments of the present invention and that modifications may be made therein without departing from the spirit or scope of the present invention as set forth in the claims. To particularly point out and distinctly claim the subject matter regarded as invention, the following claims conclude this specification.

COMPARATIVE EXAMPLE 1

Original Route

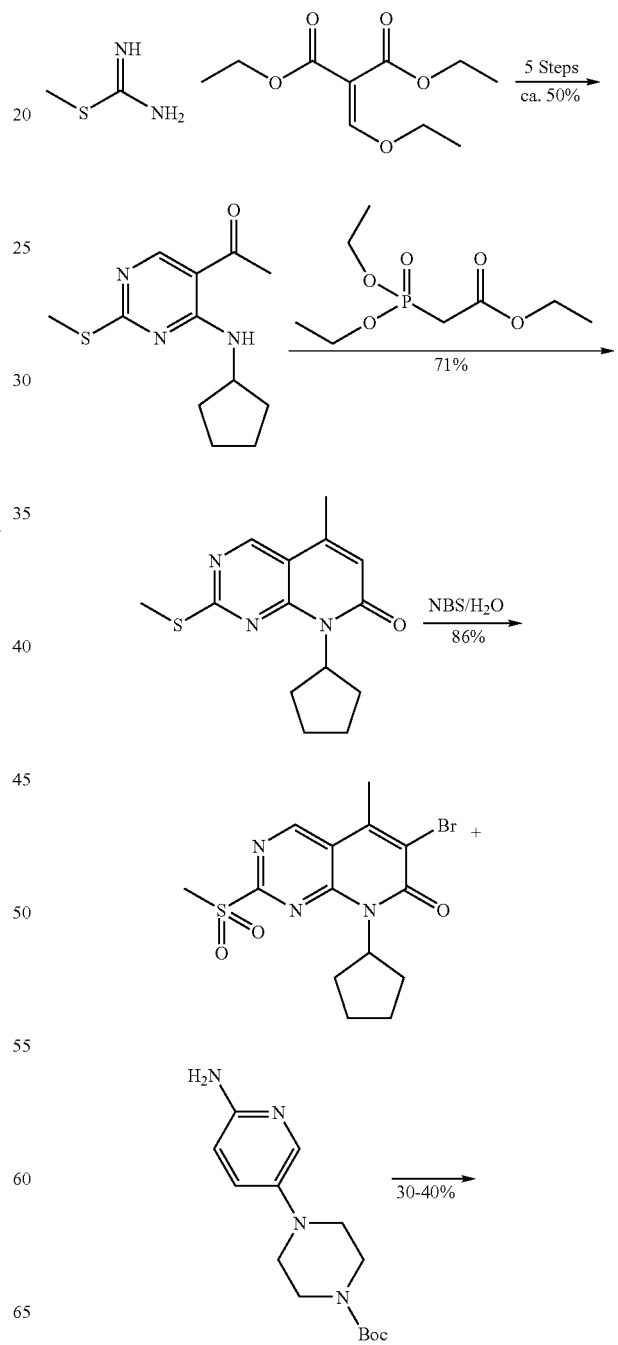

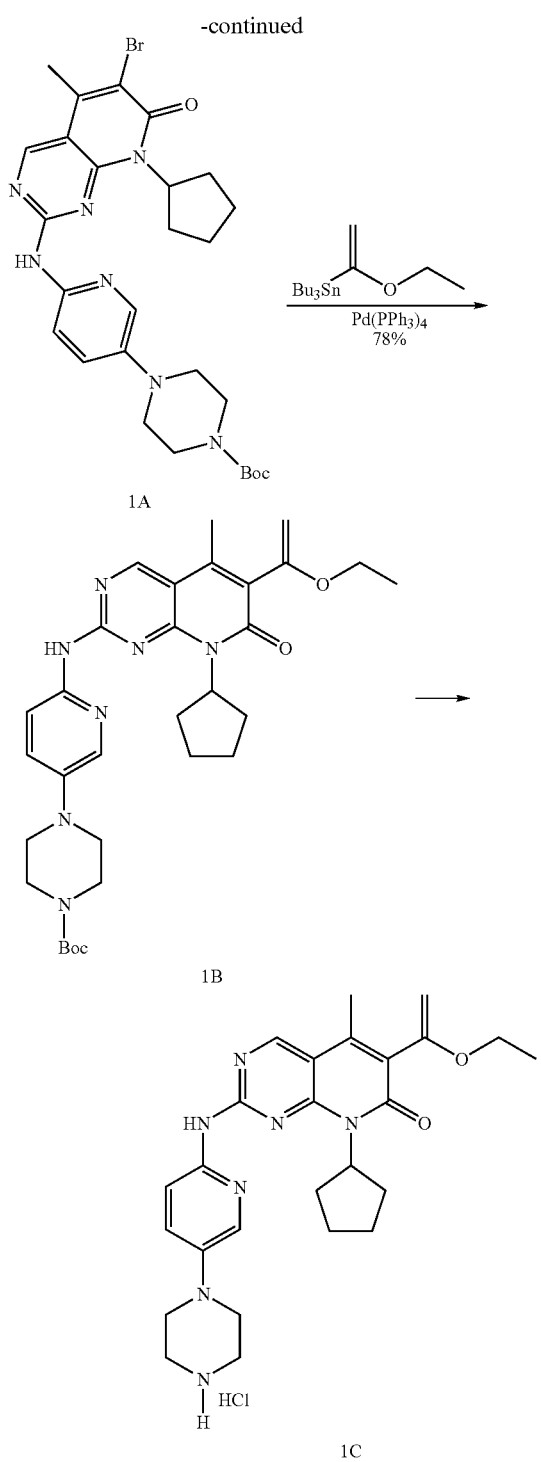

COMPARATIVE EXAMPLE 1A

Preparation of 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester A suspension of 6-bromo-8-cyclopentyl-2-methansulfinyl-5-methyl-8H-pyrido[2,3-d]pyrimidin-7-one (10.00 g, 0.027 mol, prepared as in Example 6 of WO 01/707041, which is incorporated herein by reference) and 10.37 g (0.0373 mol) of 4-(6-amino-pyridin-3-yl)-piperazine-1-carboxylic acid tert-butyl ester in toluene (100 mL) was heated under nitrogen in an oil bath for 7 hours. Thin layer chromatography (SiO$_2$, 10% MeOH/DCM) indicated the presence of both starting materials. The suspension was heated under reflux for an additional 18 hours. The resulting suspension was cooled to RT and filtered to give 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (5.93 g, 38%). Melting point>250° C. MS (APCI) M$^+$+1: calc'd, 584.2, found, 584.2.

COMPARATIVE EXAMPLE 1B

Preparation of 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-piperazine-1-carboxylic acid tert-butyl ester A suspension of 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester (5.93 g, 0.010 mol, prepared as in Example 1A), tetrakis(triphenylphosphine)palladium(0) (1.40 g, 0.00121 mol), and tributyl(1-ethoxyvinyl)tin (5.32 mL, 0.0157 mol) in toluene (30 mL) was heated under reflux for 3.5 hours. The mixture was cooled and filtered to give a solid. Purification of the solid by silica gel chromatography using a gradient of 5%-66% ethyl acetate/hexane over 15 minutes gave 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-piperazine-1-carboxylic acid tert-butyl ester as a yellow foam (4.50 g, 78%). MS (APCI) M$^+$+1: calc'd 576.2, found, 576.3.

COMPARATIVE EXAMPLE 1C

Preparation of 6-acetyl-8-cyclopentyl-5-methyl-2-(5-piperazin-1-yl-pyridin-2-ylamino)-8H-pyrido[2,3-d]pyrimidin-7-one hydrochloride Hydrogen chloride gas was bubbled into an ice-bath cooled solution of 4-{6-[8-cyclopentyl-6-(1-ethoxy-vinyl)-5-methyl-7-oxo-7,8-dihydro-pyrido[2,3-d]pyrimidin-2-ylamino]-pyridin-3-yl}-piperazine-1-carboxylic acid tert-butyl ester (4.50 g, 0.00783 mol, prepared as in 2005-0059670A1) in DCM (100 mL). The resulting suspension was stoppered and stirred at RT overnight, then diluted with diethyl ether (200 mL). The solid was collected by filtration, washed with diethyl ether, and dried to give the hydrochloride salt of 6-acetyl-8-cyclopentyl-5-methyl-2-(5-piperazin-1-yl-pyridin-2-ylamino)-8H-pyrido[2,3-d]pyrimidin-7-one as a yellow solid (4.01 g, 92%). Melting point 200° C. HPLC, C18 reverse phase, 10%-95% gradient of 0.1% TFA/CH$_3$CN in 0.1% TFA/H$_2$O during 22 minutes: 99.0% at 11.04 minutes. MS (APCI) M$^+$+1: calc'd, 448.2, found, 448.3. Anal. calc'd for C$_{24}$H$_{29}$N$_7$O$_2$.2.4H$_2$O.1.85 HCl: C, 51.64; H, 6.44; N, 17.56, Cl (total), 11.75. Found: C, 51.31; H, 6.41; N, 17.20; Cl (total), 12.11.

EXAMPLE 2

Preparation of 4-(6-Nitro-pyridin-3-yl)-piperazine-1-carboxylic acid tert-butyl ester

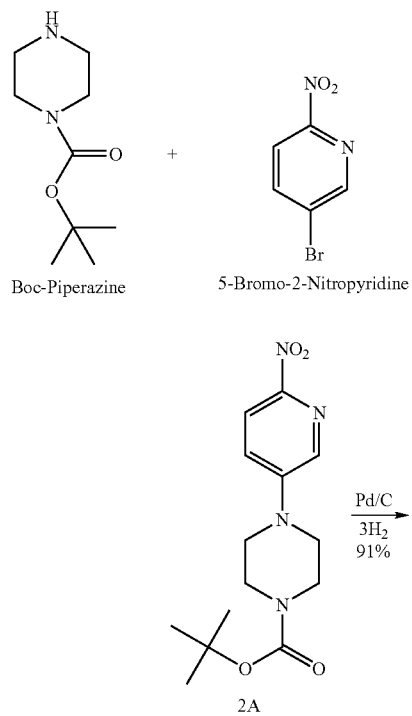

EXAMPLE 2A

Preparation of 4-(6-Nitro-pyridin-3-yl)-piperazine-1-carboxylic acid tert-butyl ester To 1.0 kg (5 mol) 5-bromo-2-nitropyridine was added 1.2 kg (6.4 mol) boc piperazine (tert-Butyl piperazine-1-carboxylate) in 2.6 L DMSO and 0.5 kg triethylamine under nitrogen. The mixture was heated to 65-70° C. and held for 30 hours after which some solids precipitated. Water was added and the reaction cooled to 25° C. over 2 hrs. The resulting slurry was filtered, washed and dried at 45° C. to give 1.2 kg (79% crude yield) of canary yellow solid intermediate (2A), which was used without further purification in the subsequent step.

EXAMPLE 2

Preparation of 4-(6-Nitro-pyridin-3-yl)-piperazine-1-carboxylic acid tert-butyl ester (2)

60.0 g of 20% Pd(OH)$_2$/C, 1213.1 g (3.9 moles) of intermediate 2a, and isopropanol were charged and stirred in a Parr reactor, then purged under gas, followed by removal of the catalyst under pressure. The filtrates were concentrated in vacuo at ~20° C. leaving 917 g of dry brown powder (crude yield ~84%).

EXAMPLE 3

Preparation of 2-Chloro-8-cyclopentyl-5-methyl-8H-pyrido[2,3-d]pyrimidin-7-one

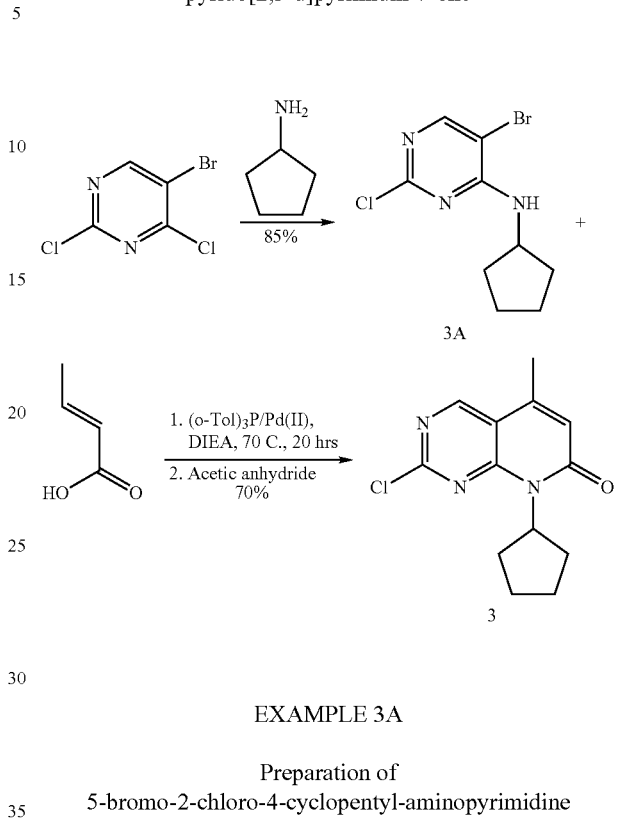

EXAMPLE 3A

Preparation of 5-bromo-2-chloro-4-cyclopentyl-aminopyrimidine

To 1 g (0.004 mol) of 5-bromo-2,4-dichloropyrimidine in ethanol was added 1.5 kg (0.018 mol) cyclopentylamine under nitrogen. The mixture was stirred at 25° C. for 2 hrs. Water was added to precipitate the product, and the solid was recrystallized using hexane 4:1 to give a white crystalline product (3A).

EXAMPLE 3

Preparation of 2-Chloro-8-Cyclopentyl-5-methyl-8H-pyrido[2,3-d]pyrimidin-7-one 41.5 g (0.15 mol) of 5-bromo-2-chloro-4-cyclopentylaminopyrimidine 3a and 32.3 g (0.375 mol) of crotonic acid were mixed in 100 L of THF and 105 ml (1.6 mol) diisopropyl ethylamine under nitrogen. The slurry was stirred, evacuated and refilled with nitrogen three times, after which 860 mg (0.0022 mol) palladium dichloride dibenzonitrile complex and 685 mg (0.0022 mol) tri-ortho-tolylphosphine were added and the resulting slurry degassed an additional three times. The mixture was then heated and stirred at 70° C. for 16 hrs, after which 35 ml acetic anhydride was added and the mixture stirred for an additional 1.5 hrs. The mixture was cooled and diluted with 100 ml MTBE and then extracted with 1NHCl, then aqueous sodium bicarbonate and brine. The organic phase was dried over magnesium sulfate, filtered, concentrated in vacuo, and recrystallized from IPA to yield 31.2 g (68%) of crude product (3).

EXAMPLE 4

4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester

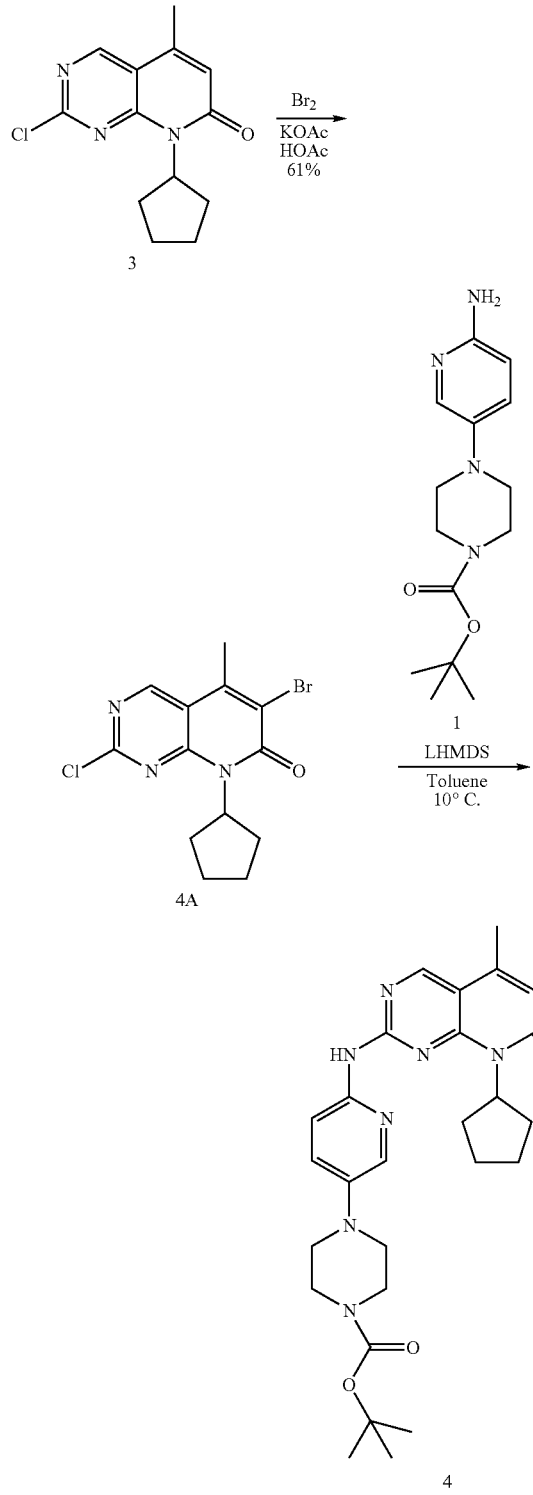

EXAMPLE 4A

Preparation of 2-chloro-8-cyclopentyl-5-methyl-8H-pyrido[2,3-d]pyrimidine-7-one 10 g (0.04 mol) of intermediate 3 and 13 g (0.16 mol) of sodium acetate were mixed with 50 ml of glacial acetic acid and 12 g (0.08 mol) bromine under nitrogen. The solution was heated to 50° C. and stirred for 35 hrs, then cooled to room temperature. Sodium bisulfite solids were added until the bromine color disappeared, then quenched, filtered and washed to provide a solid which was subsequently dissolved in 500 ml hot IPA, filtered hot, and cooled. The resulting crystals were further filtered, and dried in vacuo at 65° C. to yield 8 g (61%) of crude product (4A).

EXAMPLE 4

Preparation of 4-[6-(6-bromo-8-cyclopentyl-5-methyl-7-oxo-7,8-dihydro-pyrido[2,3-d]pyrimidin-2-ylamino)-pyridin-3-yl]-piperazine-1-carboxylic acid tert-butyl ester 3.78 g (2.10 equiv; 13.6 mmoles) of intermediate 1, 25 ml toluene and lithium bis(trimethylsilyl)amide in 1 M THF (13.6 mmoles; 13.6 mL; 12.1 g) were mixed for 10 min under nitrogen to form a dark solution. In a separate beaker the intermediate 4a (1.00 equiv, 6.47 mmoles; 2.50 g) was slurried in toluene then added to the mixture containing 1 and stirred for 30 min, after which the combined mixture was quenched with 25 ml 1 M sodium bicarbonate and then filtered. Alternatively, the combined mixture can be quenched with ammonium chloride. The filter cake was washed with toluene, then acetone, then water and dried at 60° C. to give 3.5 g (92%) of a grey-yellow solid 4.

EXAMPLE 5

Preparation of 4-{6-[6-(1-butoxy-vinyl)-8-cycloentyl-5-methyl-7-oxo-7,8-dihydropyrido[2,3-d]pyrimidin-2-ylamino]-pyridin-3-yl}-piperazine-1-carboxylic acid tert-butyl ester

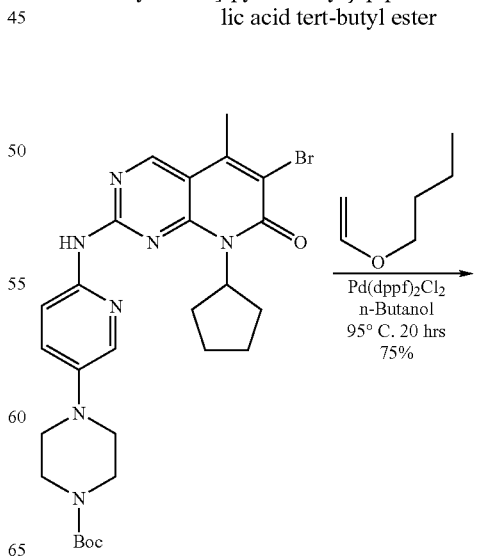

-continued

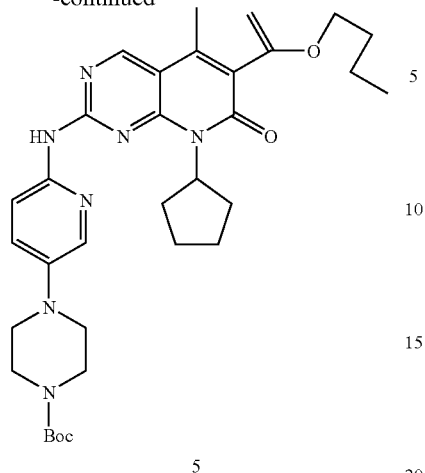

5

-continued

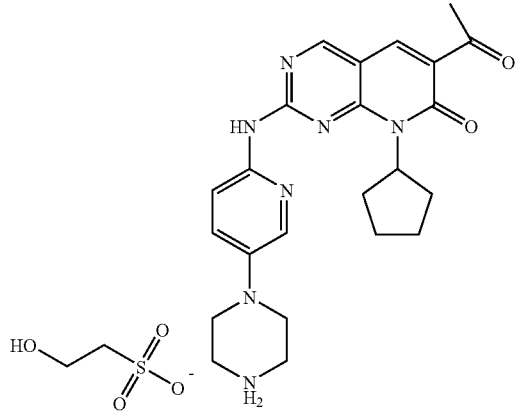

768 g (1.3 mol) of intermediate 4, was mixed with 395 g (3.9 mol) of butyl vinyl ether, 4.7 L of n-butanol, and 275 ml (1.6 mol) diisopropyl ethylamine under nitrogen. The slurry was stirred and placed under ca. 50 tore vacuum and then refilled with nitrogen; this was repeated 2 more times. To this degassed solution was added 22 g (0.03 mol) Bis-(diphenylphosphinoferrocene)palladium dichloride dichloromethane complex and the resulting slurry was degassed an additional three times as described above. The mixture was then heated and stirred at 95° C. for 20 hrs. The resulting thin red slurry was diluted with 4 L branched octane's and cooled to about 5° C. after which 1 L saturated aq. potassium carbonate was added and the mixture was filtered and rinsed with 500 ml branched octanes. After drying for 16 hrs at 45° C., 664 g (83%) of gray-solid product (5) was obtained. In addition, column chromatography can be used to further purify the crude product.

EXAMPLE 6

Preparation of 6-acetyl-8-cyclopentyl-5-methyl-2-(5-piperazin-1-yl-pyridin-2-ylamino)-8H-pyrido[2,3-d]pyrimidin-7-one

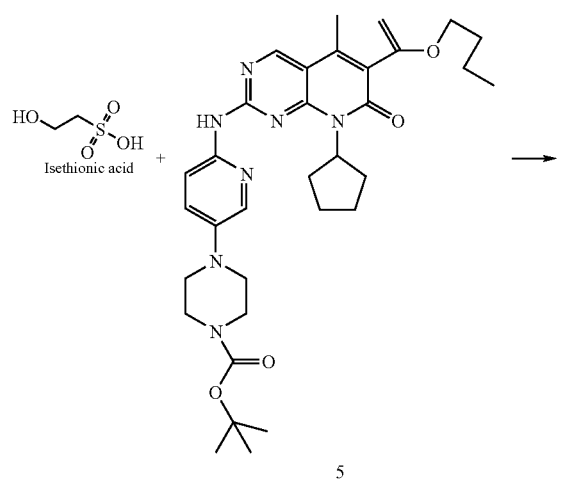

5

11.6 g (1.00 eq, 19.2 mmol) of intermediate 5, water (10.1 equiv; 193 mmoles; 3.48 mL; 3.48 g) and methanol (3.62 moles; 146 mL; 116 g) were combined and heated to 55-60° C. Isethionic acid was added slowly until a clear solution was obtained; 3.3 g isethionic acid solution was necessary to reach this end point. The resulting clear orange solution was filtered through paper and rinsed through with 20 ml methanol, after which the filtrate was reheated to 55-60° C. and the remaining isethionic acid was added (a total of 9.93 g was added). The reaction mixture precipitated and thickened for 6 hours, after which it was cooled and held at 30-35° C. while triethylamine (2.92 g; 28.8 mmoles) was added slowly as a 10% solution in methanol over 12 hrs. About halfway through the addition of triethylamine, desired polymorphic seeds were added to help formation of the desired polymorph. The resulting slurry was cooled and held at 5° C. for 15 minutes and the crystals were filtered and washed with methanol. The solid product was dried in vacuo at 55° C. to obtain 11 g of yellow crystals of the title compound.

What is claimed is:

1. A method of producing a compound of formula Ic

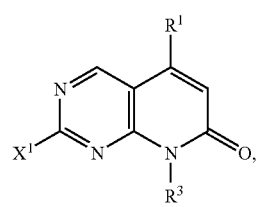

wherein $X^1$ is Cl;

$R^1$ is hydrogen, $C_1$-$C_6$ alkyl, $C_1$-$C_6$ haloalkyl, $C_1$-$C_6$ hydoxyalkyl, or $C_3$-$C_7$ cycloalkyl; and $R^3$ is hydrogen, OH, —$NH_2$, aryl, $C_1$-$C_8$ alkyl, $C_3$-$C_7$ cycloalkyl, or $C_3$-$C_7$-heterocyclyl;

comprising the steps of (g) reacting a compound of formula Ib:

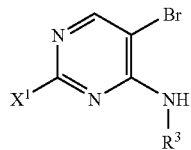

Ib with a compound of the formula

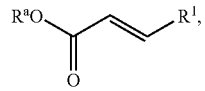

wherein $R^a$ is selected from H, $C_1$-$C_3$ alkyl and —C(O)—$C_1$-$C_3$alkyl, in the presence of diisopropylethylamine, a transition metal catalyst selected from tetrakis(triphenylphosphine)palladium, tris(dibenzylideneacetone) dipalladium, bis(dibenzylideneacetone) palladium(0), palladium acetate, palladium chloride, bis(benzonitrile) dichloropalladium and (Bis-(diphenylphosphinoferrocene) palladium dichloride dichloromethane complex and optionally a phosphine agent selected from 2,2'-bis(diphenylphosphino)-1,1'-binaphthalene, 1,3 bis(diphenylphosphino)propane, triphenylphosphine, triorthotolylphosphine and tri-t-butylphosphine, and in a suitable solvent selected from toluene and THF;

to produce the compound of formula Ic.

2. A method of preparing a compound of formula Ic

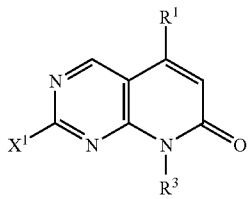

Ic wherein $R^1$ is hydrogen, $C_1$-$C_6$ alkyl, $C_1$-$C_6$ haloalkyl, $C_1$-$C_6$ hydroxyalkyl, or $C_3$-$C_7$ cycloalkyl;

$R^3$ is hydrogen, OH, —$NH_2$, aryl, $C_1$-$C_8$ alkyl, $C_3$-$C_7$ cycloalkyl, or $C_3$-$C_7$-heterocyclyl; and comprising the steps of (a) reacting a compound of formula Ib:

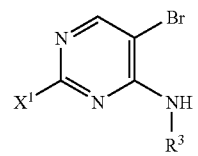

Ib with a compound of the formula

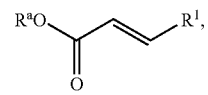

wherein $R^a$ is selected from H, $C_1$-$C_3$ alkyl and —C(O)—$C_1$-$C_3$alkyl, in the presence of diisopropylethylamine, a transition metal catalyst selected from tetrakis(triphenylphosphine)palladium, tris(dibenzylideneacetone) dipalladium, bis(dibenzylideneacetone) palladium(0), palladium acetate, palladium chloride, bis(benzonitrile) dichloropalladium and (Bis-(diphenylphosphinoferrocene) palladium dichloride dichloromethane complex, and optionally a phosphine agent selected from 2,2'-bis(diphenylphosphino)-1,1'-binaphthalene, 1,3 bis(diphenylphosphino)propane, triphenylphosphine, triorthotolylphosphine and tri-t-butylphosphine, and in a suitable solvent selected from toluene and THF; and (b) treating the resulting product of step (a) with acetic anhydride to produce a compound of formula Ic.

\* \* \* \* \*